US011496071B2

United States Patent
Makdissi et al.

(10) Patent No.: US 11,496,071 B2
(45) Date of Patent: Nov. 8, 2022

(54) PIEZOELECTRIC TRANSDUCER-BASED ENERGY HARVESTING MODULE, IN PARTICULAR FOR OPTIMIZED CHARGING OF THE BATTERY OF AN IMPLANTABLE MEDICAL DEVICE SUCH AS A LEADLESS AUTONOMOUS CARDIAC CAPSULE

(71) Applicant: CAIRDAC, Antony (FR)

(72) Inventors: Alaa Makdissi, Paris (FR); An Nguyen-Dinh, La Riche (FR)

(73) Assignee: CAIRDAC, Antony (FR)

( * ) Notice: Subject to any disclaimer, the term of this patent is extended or adjusted under 35 U.S.C. 154(b) by 135 days.

(21) Appl. No.: 17/192,754

(22) Filed: Mar. 4, 2021

(65) Prior Publication Data

US 2021/0408945 A1  Dec. 30, 2021

(30) Foreign Application Priority Data

Jun. 24, 2020 (EP) ..................................... 20315317

(51) Int. Cl.
*H02N 2/18* (2006.01)
*H01L 41/047* (2006.01)
*H01L 41/113* (2006.01)

(52) U.S. Cl.
CPC ......... *H02N 2/188* (2013.01); *H01L 41/0471* (2013.01); *H01L 41/1136* (2013.01); *H02N 2/181* (2013.01)

(58) Field of Classification Search
CPC . H01L 41/1136; H01L 41/0471; H02N 2/181; H02N 2/188
See application file for complete search history.

(56) References Cited

U.S. PATENT DOCUMENTS

| 8,311,632 | B2 * | 11/2012 | Pless .................... H02N 11/002 607/35 |
| 11,205,977 | B2 * | 12/2021 | Okada .................... H02N 2/181 |
| 11,229,800 | B2 * | 1/2022 | Makdissi ............... H02N 2/188 |
| 11,357,994 | B2 * | 6/2022 | Regnier .............. H01L 41/1136 |
| 2007/0167988 | A1 | 7/2007 | Cernasov |
| 2009/0174289 | A1 | 7/2009 | Tanner |
| 2015/0015114 | A1 | 1/2015 | Hall et al. |
| 2017/0110989 | A1 | 4/2017 | Okada et al. |

FOREIGN PATENT DOCUMENTS

WO  WO2019001829  1/2019

* cited by examiner

*Primary Examiner* — J. San Martin
(74) *Attorney, Agent, or Firm* — CRGO Global; Steven M. Greenberg (57) ABSTRACT

The module comprises a pendular unit with an elastically deformable piezoelectric beam having a clamped end and an opposite, free end, coupled to an inertial mass. The beam produces an oscillating electrical signal collected by electrodes, which is rectified and regulated to output a voltage for charging a battery. The number and configuration of the electrodes (T1, T2, B1, B2, N) carried by the piezoelectric beam define a plurality of pairs of electrodes between which a corresponding plurality of said oscillating signals can be simultaneously collected. A switching matrix, as a function of an input command, selectively switches the plurality of pairs of electrodes between each other according to a plurality of different series (S), parallel (P) and/or series-parallel (SP) configurations, the selected configuration being that which maximizes the power sent to the battery as a function of the voltage level (VBAT) present at the terminals of the latter.

11 Claims, 6 Drawing Sheets

PIEZOELECTRIC TRANSDUCER-BASED ENERGY HARVESTING MODULE, IN PARTICULAR FOR OPTIMIZED CHARGING OF THE BATTERY OF AN IMPLANTABLE MEDICAL DEVICE SUCH AS A LEADLESS AUTONOMOUS CARDIAC CAPSULE

CROSS REFERENCE TO RELATED APPLICATIONS

This application claims priority under 35 U.S.C. § 119(a) to European patent application 20315317.6 filed on Jun. 24, 2020, the entire teachings of which are incorporated herein by reference.

BACKGROUND OF THE INVENTION

Field of the Invention

The invention relates to energy harvesting devices, also called harvesters or scavengers, which collect mechanical energy resulting from various movements they undergo and convert this mechanical energy into electrical energy.

It more particularly relates to the harvesting devices of the so-called "PEH" (Piezoelectric Energy Harvester) type, which use as a mechanical-electrical transducer an oscillating piezoelectric beam coupled to an inertial mobile mass.

The invention will be more particularly described in an application of such energy harvesters to autonomous medical devices, in particular devices of the autonomous implantable capsule type, in particular those which are intended to be implanted in a heart cavity.

This application, although being particularly advantageous, must however not be considered as limitative of the invention, whose teachings can be applied to many other types of autonomous devices incorporating an energy harvester of the PEH type, whether these devices are implantable or not, medical devices or not.

Description of the Related Art

In the field of medical implants, recent advances in miniaturization of active devices and advances in life sciences allow from now on the development of a wide variety of fully autonomous, miniaturized implantable systems, for monitoring, diagnosis or treatment purposes. Such devices implement less invasive implantation procedures, provide more comfort, increased performances, and often open up access to new types of diagnoses and treatments.

When applied to the field of medical implants, the invention more particularly relates to those devices which incorporate a self-powering system comprising a mechanical energy harvester associated with an integrated energy storage component, such as a rechargeable battery or a high-performance capacitor.

Indeed, one of the critical aspects of these miniaturized devices is the power autonomy. The life duration of such an implant being of about 8-10 years, taking into account the very small dimensions, it is not possible to use a conventional battery, even a high-density one.

The energy harvesting device, also called harvester or scavenger, addresses this drawback by collecting the mechanical energy resulting from the various movements undergone by the body of the implanted device. Those movements may have for origin a certain number of phenomena occurring for example at the rhythm of the heartbeats, such as periodic shakes of the wall on which the implant is anchored, heart tissue vibrations linked i.a. to closings and openings of the heart valves, or also blood flow rate variations in the surrounding environment, which stress the implant and make it oscillate at the rhythm of the flow rate variations.

The mechanical energy collected by the harvester is converted into electrical energy (voltage or current), by means of a suitable mechanical-electrical transducer, for powering the various circuits and sensors of the device and charging the energy storage component. This power supply system allows the device to operate in full power autonomy for its whole lifetime.

This energy harvesting technique is particularly well adapted for powering the implanted autonomous capsules having no physical connection with a remote device. Such capsules are called for this reason "leadless capsules", for distinguishing them from the electrodes or sensors arranged at the distal end of a lead, through the whole length of which run one or several conductors connected to a generator itself connected to the opposite, proximal end.

The invention is nevertheless not limited to a particular type of capsule, nor even of leadless implant, and is applicable as well to many other types of implantable medical devices, whatever the operational purpose thereof, cardiac or other, medical or not.

In the cardiac application case, the leadless capsule continuously monitors the rhythm of the patient and if necessary issues to the heart electrical pulses for pacing, resynchronization and/or defibrillation in case of rhythm disorders detected by the capsule. The capsule further comprises various electronic circuits, sensors, etc., as well as wireless communication transmission/reception means for the remote exchange of data, the whole being integrated in a very small size body able to be implanted at sites of difficult access or leaving little available space, such as the ventricle apex, the inner wall of the atrium, etc.

WO 2019/001829 A1 (Cairdac) describes an example of such a leadless intracardial capsule.

The invention more particularly relates to capsules or similar implantable devices whose energy harvester is of the PEH type, i.e. using a PieZoelectric Transducer or "PZT" and an inertial pendular unit subjected to the above-described external stresses. The inertial pendular unit comprises, within the capsule body, a mobile mass called "seismic mass" or "inertial mass", which is driven according to the movements of the capsule, permanently subjected to the various external stresses described hereinabove. After each of these stresses, the inertial mass, which is coupled to an elastically deformable element, oscillates at a natural free oscillation frequency.

The mechanical energy of the oscillation is converted into electrical energy by a mechanical-electrical transducer producing an electrical signal. This mechanical-electrical transducer may in particular by a PZT that is cyclically and alternately stressed in bending so as to generate within its constituent material electrical charges that are collected at the surface of the component to be used by the self-powering system of the leadless capsule. The PZT may in particular be a piezoelectric beam clamped at one of its end and coupled to the inertial mass at its other end, which is free.

The transducer output electrical signal is sent to a power management circuit of the capsule, which rectifies and regulates the electrical signal to output a stabilized direct voltage or current, usable to power the various electronic circuits and sensors of the capsule, and to charge the energy storage component.

Such a PEH harvester is described in particular in U.S. Pat. No. 3,456,134 A (Ko) and in above-mentioned WO 2019/001829 A1.

US 2015/015114 A1 (Hall et al.) also describes a PEH harvester, in which a substrate carries a plurality of distinct elongated PZT transducers, parallel to each other, arranged in the same direction as the main bending direction of the substrate or perpendicularly to this direction, and that may be switched as a function of the amplitude of vibration of the beam or of the different vibration modes of the latter, to form at will a series, or parallel, array of transducers.

It will be noted that the term "beam" has to be understood in its broadest sense, i.e. an elongated, thin and flat strip, it being understood that the shape of this strip is not necessarily rectangular nor its thickness constant (as in the description of the particular embodiment that will be given hereinafter). Within the meaning of the present invention, the term "beam" hence covers elements that may have a non-constant width and/or thickness in the longitudinal direction, as well as, possibly, a deformability liable to exceed a unique degree of freedom in bending.

However, the electrical signal produced by the piezoelectric beam cannot be used directly to power the various electronic circuits and sensors of the capsule and charge the energy storage component (rechargeable battery or other storage means such as a high-performance capacitor, hereinafter referred to by the generic term "battery").

For that purpose, the damped oscillating electrical signal collected at the piezoelectric beam terminals is sent as an input to a power management circuit of the capsule, usually called "PMU" (Power Management Unit). This circuit rectifies and regulates the oscillating electrical signal and outputs a stabilized voltage or current usable to power the electric circuits of the implant and to charge the battery.

Using a PZT as a power source makes this power management particularly complex.

Indeed, from the electrical point of view, the PZT can be equated to a source of alternative current of variable amplitude having a high, essentially capacitive, internal impedance. Actually, to optimize the energy extraction while minimizing the losses, the PMU must be able to dynamically follow the voltage variation at the PZT terminals and to discharge in the most suitable way the charges accumulated in the internal capacitor in order to minimize the losses by self-discharge within the PZT.

On the other hand, after rectification, the battery charging current must be controlled as a function of the voltage at the battery terminals, this voltage varying as a function of the battery level and the instantaneous electric charge, which represents the consumption of the implant electric circuits. Concretely, the charging power available at the PMU output can be represented by a power/voltage characteristic that increases for low values of the battery voltage, passes by a maximum, then decreases for high values of the battery voltage, the voltage produced by the PZT then becoming lower than the voltage at the battery terminals and no longer enabling it to be charged.

This problem, which is specific to the use of a PZT as a primary power source for charging a battery, makes the power management very tricky, so that the use of a dedicated complex circuit of the ASIC type is required to ensure the PMU functions.

A particularly suitable ASIC type implements SSHI (Synchronized Switch Harvesting on Inductor) circuits. Theses SSHI circuits are efficient but, due to their complexity, cause a non-negligible consumption, which is hence detrimental to the implant autonomy. Moreover, in the case of an SSHI circuit, the presence of an inductor in the PMU makes the latter sensitive to the high magnetic fields undergone by the patient, and hence by the implant, during magnetic resonance imaging (MRI) scans, with risks of disturbance of the circuit operation, or even degradation of the latter due to overcurrent or internal heating. Moreover, the size of a inductor having a high quality factor is not compliant with the extreme miniaturization required by a leadless capsule.

One of the objects of the invention is to propose a PEH configuration that addresses these multiples drawbacks and constraints, with an oversimplified PMU, devoid of any inductive component, whose own consumption is negligible, and which, moreover and above all, maximizes the energy harvesting over a very wide range of operating voltages of the battery.

BRIEF SUMMARY OF THE INVENTION

For that purpose, the invention proposes an energy harvesting module of the PEH type comprising, in a manner known per se, in particular from above-mentioned US 2015/015114 A1, a pendular unit subjected to external stresses applied to the module, the pendular unit comprising a beam that is elastically deformable in bending according to at least one degree of freedom, with a clamped end and an opposite free end coupled to an inertial mass. The beam is a piezoelectric beam forming a mechanical-electrical transducer adapted to convert a mechanical energy produced by oscillations of the pendular unit into an oscillating electrical signal collected by electrodes. The module also comprises a power management circuit, adapted to rectify and regulate the signal collected by the electrodes, to output a stabilized direct power voltage or current.

Characteristically of the invention, the number and configuration of the electrodes carried by the piezoelectric beam define a plurality of pairs of electrodes between which a corresponding plurality of oscillating signals can be simultaneously collected. The energy harvesting module further comprises, between the piezoelectric beam and the power management circuit, a switching matrix adapted, as a function of an input command, to selectively switch the plurality of pairs of electrodes between each other according to a plurality of different series, parallel and/or series-parallel configurations, to output a combined oscillating signal applied to the power management circuit.

According to various advantageous subsidiary features:

the power management circuit is essentially consisted of a rectification stage and a filtering stage, the stages receiving as an input the combined oscillating signal output by the switching matrix and outputting the stabilized direct voltage or current;

the piezoelectric beam is a bimorphous beam comprising a central conductive core and at least two surface electrodes on each side of the beam, the central conductive core and/or the surface electrodes being connected to the input of the switching matrix to selectively define pairs of electrodes combined to each other to produce the plurality of different series, parallel and/or series-parallel configurations;

said at least two surface electrodes are subdivided into sub-electrodes that are selectively switchable by the switching matrix in complement to said series, parallel and/or series-parallel configurations, to modify the equivalent capacitance of said electrodes in order to produce an extra voltage or power at the switching matrix output;

the switching matrix is consisted of individually controllable static switch components, in particular pairs of complementary PMOS/NMOS transistors that are symmetrically controlled in conduction or cutoff state;

the input command is function of a voltage level signal of an energy storage component coupled to the power management circuit output and charged by the stabilized direct power voltage;

in this later case, the module can comprise in particular a means for comparing the current voltage level of the energy storage component with at least two successive voltage level ranges, and wherein a transition of the current voltage level of the energy storage component from one range to another during the charge is operable to control a change of series, parallel and/or series-parallel configuration of the switching matrix. These successive ranges are advantageously ranges each corresponding to a respective series, parallel and/or series-parallel configuration maximizing the power returned by the piezoelectric beam.

The module of the invention can in particular be incorporated to an autonomous device housing, within a device body, an electronic unit, the energy harvesting module and an energy storage component for powering the electronic unit. The stabilized direct voltage or current output by the power management circuit is then used to power the electronic unit and/or to charge the energy storage component of the autonomous device.

This autonomous device can notably be an active medical device, in particular an implantable capsule comprising a capsule body provided with an anchoring element for its anchoring to a wall of an patient's organ, the external stresses to which is subjected the pendular unit of the energy harvesting module being then the stresses applied to the capsule body under the effect of movements of the wall and/or blood flow rate variations in the surrounding environment.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

An exemplary embodiment of the device of the invention will now be described, in an application to an autonomous implantable capsule intended to be implanted into a heart cavity.

As indicated hereinabove, this particular application is not limitative of the invention, whose teachings may be applied to many other types of autonomous devices incorporating an energy harvester of the PEH type, whether these devices are implantable or not, medical or not.

Figure 1:
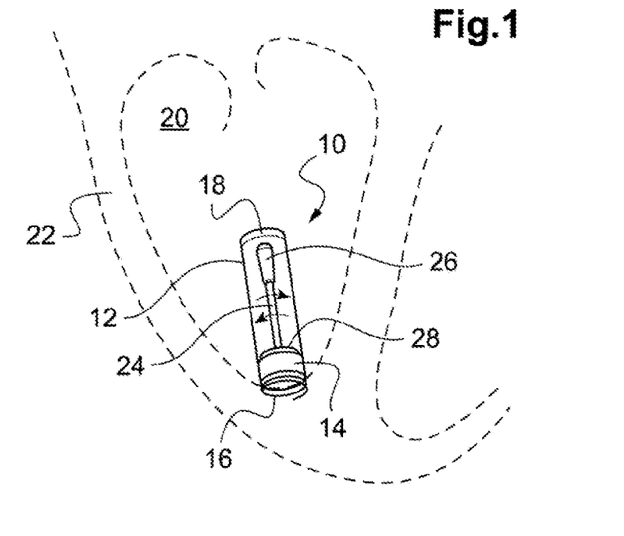
FIG. 1 illustrates a medical device of the leadless capsule type in its environment, implanted in the bottom of the right ventricle of a patient.

FIG. 1 shows a leadless capsule device 10 in an application to cardiac pacing.

Capsule 10 has the external form of an implant with an elongated cylindrical tubular envelope 12 enclosing the various electronic and power circuits of the capsule, as well as a pendular unit based energy harvester. The typical size of such a capsule is about 6 mm diameter for about 25 40 mm length.

Tubular envelope 12 has, at its front (distal) end 14, a protruding anchoring element, for example an helical screw 16, to hold the capsule on the implantation side. Other anchoring systems can be used, and do not modify in any way the implementation of the present invention. The opposite (proximal) end 18 of capsule 10 is a free end, which is only provided with means (not shown) for the temporary connection to a guide-catheter or another implantation accessory used for implantation or explanation of the capsule, which is then detached from the latter.

In the example illustrated in FIG. 1, leadless capsule 10 is an endocavitary implant implanted into a cavity 20 of myocardium 22, for example at the apex of the right ventricle. As an alternative, still in an application to cardiac pacing, the capsule can also be implanted on the interventricular septum or on an atrial wall, or also be an epicardial capsule placed on an external region of the myocardium, these different implantation modes not modifying in any way the implementation of the present invention. To perform the detection/pacing functions, an electrode (not shown) in contact with the heart tissue at the implantation site collects heart depolarization potentials and/or applies pacing pulses. In certain embodiments, the function of this electrode can be provided by anchoring screw 16, which is then an active screw, electrically conductive and connected to the detection/pacing circuit of the capsule.

Leadless capsule 10 is moreover provided with an energy harvesting module, called "PEH", comprising an inertial pendular unit that oscillates, inside the capsule, following the various external stresses to which the capsule is subjected. These stresses may result in particular from: movements of the wall to which the capsule is anchored, which are transmitted to tubular body 12 by anchoring screw 16; and/or blood flow rate variations in the environment surrounding the capsule, which produce oscillations of tubular body 12 at the rhythm of the heartbeats; and/or various vibrations transmitted by the heart tissues.

The pendular unit is consisted by a piezoelectric beam 24 clamped at one of its ends, at position 28, and whose opposite, free end is coupled to a mobile inertial mass 26. Piezoelectric beam 24 is an elastically deformable flexible beam that constitutes, with inertial mass 26, a pendular system of the mass-spring type. Due to its inertia, mass 26 subjects beam 24 to a deformation of the vibratory type on either side of a neutral or non-deformed position corresponding to a stable rest position in the absence of any stress.

Actually, as for its mechanical behavior, this unit may be equated to a "clamped/free beam structure", having a natural oscillation frequency, which is herein the frequency at which the mass-spring system oscillates. It will be noted that this natural oscillation frequency, typically of the order of a few tens of hertz, is noticeably higher than the frequency of the external cyclic stresses that correspond to the heartbeat frequency (at most a few hertz). Hence, at each heart contraction, the inertial mass (or other functionally similar mechanical component) will be stressed with a higher or lower amplitude, then the pendular system will oscillate several times with decreasing amplitudes (bounces characteristic of a damped periodic oscillation), and will finally stabilize up to the following heartbeat, where the stress/oscillation cycle will be comparably repeated.

Beam 24 further performs, by piezoelectric effect, a mechanical-electrical transducer function making it possible to convert into electrical charges the mechanical bending stress that is applied to it. These charges are collected by electrodes at the surface of the beam to produce an electrical signal that, after rectification, stabilization and filtering, will power the various electronic circuits of the capsule.

The beam is advantageously a beam of the bimorphous type, i.e. capable of generating energy on its two faces when subjected to a deformation. Theses transduction properties are typical of a piezoelectric material, such as PZT ceramics or PMN-PT, barium titanate or lithium niobate monocrystals.

Figure 2:
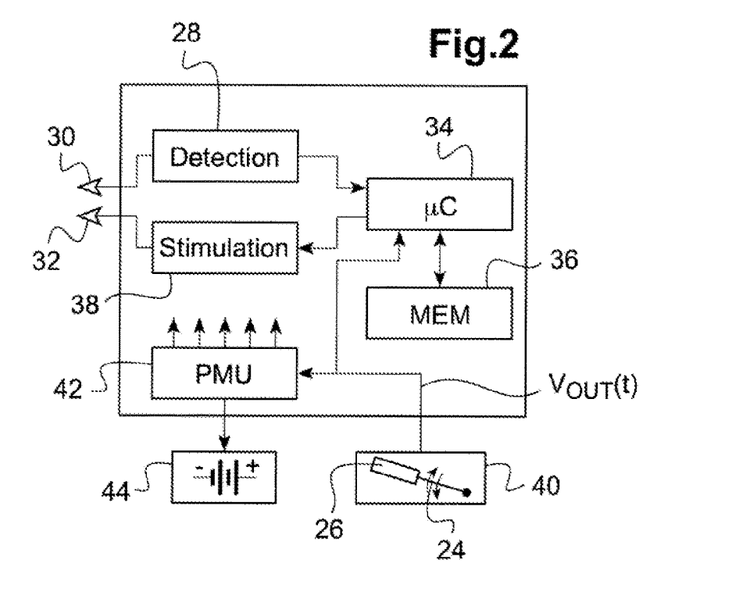
FIG. 2 schematically shows the main functional blocks constituting the leadless capsule.

FIG. 2 is a synoptic view of the various electric and electronic circuits integrated to the leadless capsule, presented as functional blocks.

Figure 4:
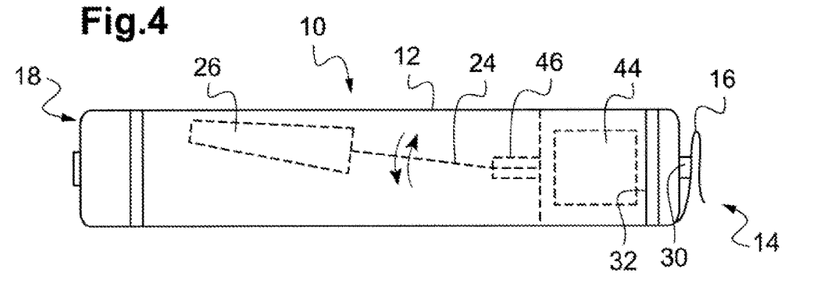
FIG. 4 is a side view of the capsule of the invention, with the main mechanical elements of the PEH pendular unit.

Block 28 denotes a heart depolarization wave detection circuit, which is connected to a cathode electrode 30 in contact with the heart tissue and to an associated anode electrode 32, for example a ring electrode formed on the tubular body of the capsule (see FIG. 4). Detection block 28 comprises filters and means for analog and/or digital processing of the collected signal. The so-processed signal is applied to the input of a microcomputer 34 associated with a memory 36. The electronic unit also includes a pacing circuit 38 operating under the control of microcomputer 34 to issue, as needed, to the electrode system 30, 32 myocardial pacing pulses.

Figure 3:
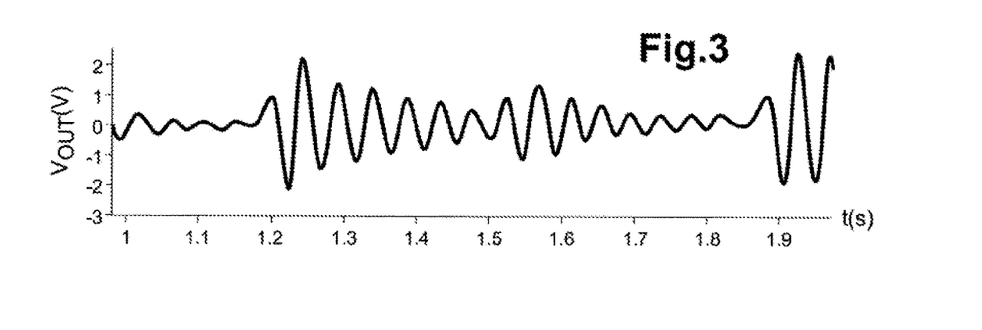
FIG. 3 is an example of damped oscillating signal output by the PEH during a cardiac cycle.

It is moreover provided an energy harvesting circuit or PEH 40, consisted by the pendular unit formed by piezoelectric beam 24 and inertial mass 30, described hereinabove with reference to FIG. 1. As piezoelectric beam 24 also ensures a mechanical-electrical transducer function, it converts into electrical charges the mechanical stresses undergone and produces a variable electrical signal VOUT(t) whose variations are illustrated in FIG. 3, which is an alternating signal oscillating at the natural oscillation frequency of the pendular beam 24/mass 30 unit, and at the rhythm of the successive beats of the myocardium to which the capsule is coupled.

The variable electrical signal VOUT(t) is sent to a power management circuit or PMU 42. PMU 42 rectifies and regulates the signal VOUT(t) so as to output a stabilized direct voltage or current serving to power the various electronic circuits and to charge the integrated battery 44.

FIG. 4 illustrates the mechanical arrangement of the just-described various components inside the cylindrical body 12 of leadless capsule 10, with in particular beam 24, whose free end is integral with the inertial mass 26, and whose opposite end is attached to the capsule body by a clamp 46, the unit being equatable, as explained hereinabove, to a "clamped/free beam" structure.

Figure 5:
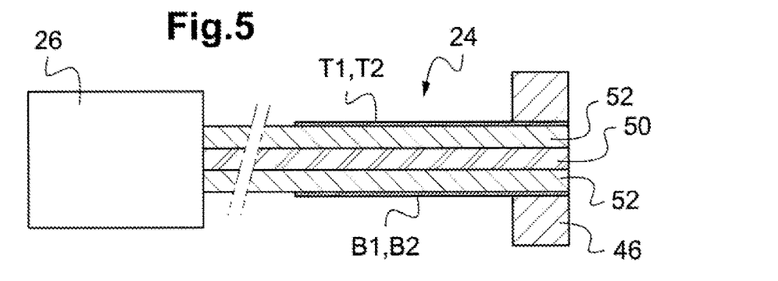
FIG. 5 is a sectional view showing, with a purposely exaggerated thickness scale, the structure of the different layers of a bimorphous PZT usable with the present invention.
Figure 6:
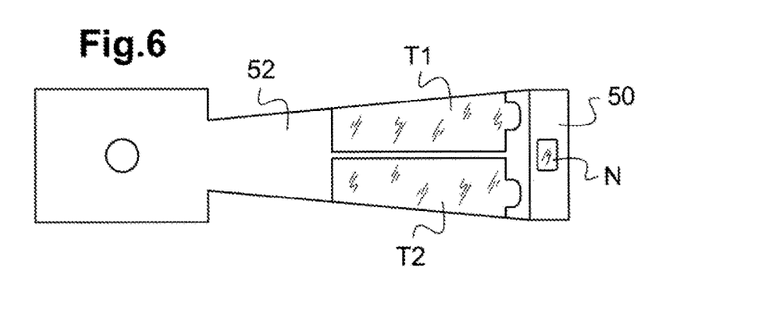
FIGS. 6 and 7 are plan views of the front and back, respectively, of a PZT usable for implementing the present invention, with a beam provided with split surface electrodes.
Figure 7:
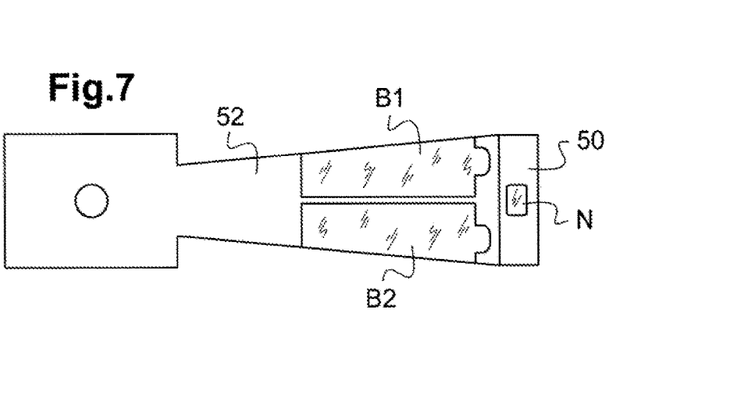

FIG. 5 schematically illustrates, with a purposely exaggerated thickness scale, the structure of the different layers of a bimorphous piezoelectric beam usable for implementing the present invention, with the two front and back sides of the beam illustrated in isolation in the respective plan views of FIGS. 6 and 7.

The beam 24 used is a bimorphous beam, i.e. comprising two layers 52 of PZT ceramic material applied on each of the opposite faces of a central core or "shim" 50 made of a conductive material (or, as an alternative, of an isolating material, with contact bridges making it possible to shunt the internal electrodes of the piezoelectric layers). This bimorphous structure actually corresponds to the association of two monomorphous structures placed back-to-back, with sharing of the core supporting the PZT material. On the other hand, in the case of the present invention, the core 50 is a core made of a conductive material, so that it is possible to collect the charges produced by the deformation of the PZT material as well between the conductive core and an surface electrode of either one or both of the PZTs, as between the two surface electrodes of the opposite faces of the beam, independently of the central core.

FIGS. 6 and 7 are plan views of the front and the back, respectively, of a PZT usable for implementing the present invention, with a beam provided with split surface electrodes.

In order to reinforce the reliability of beam 24, the shape thereof in plan view is advantageously, as illustrated, a trapezoidal shape with a (linear or exponential) decrease of the width for a better distribution of the stresses along the beam, these stresses being stronger near and at clamp 46, and null at inertial mass 26. Moreover, the trapezoidal shape makes it possible to adjust the resonant frequency of the unit as a function of the trapezoidal geometry, while maximizing the amplitude of displacement of the mass due to the fact that the free end is narrower than the clamped end.

Advantageously, and characteristically of the invention, either one or both of the surface electrodes (in the illustrated example, both surface electrodes) are split into two sub-electrodes electrically isolated from each other, i.e. electrodes T1 and T2 on the top face and, likewise, B1 and B2 on the bottom face. These four sub-electrodes each include a respective pad for the contact and the connection to the circuits of PMU 42; central core 50 also includes a corresponding contact pad N, used as a "neutral" electrical reference potential.

I will be noted that, in the figures, each surface electrode is split into two sub-electrodes substantially symmetrical to each other with respect to a central longitudinal axis of the beam. However, this configuration must not be in any case considered as limitative, many other splitting configurations being also conceivable, as well as a splitting of each electrode, or each of the electrodes, into more than two sub-electrodes, or also the splitting of only one of the two electrodes.

The beam hence includes five distinct points of electrical connection T1, T2, B1, B2 and N.

The basic idea of the invention consists in defining from these various points of connection a plurality of pairs of electrodes between which a corresponding plurality of oscillating signals resulting from the charges produced by the PZT material of the two layers 52 can be simultaneously collected, and in dynamically switching between each other these different pairs of electrodes of the plurality of pairs of electrodes so as to define several possible configurations, resulting from different couplings of these pairs of electrodes between each other, to output a combined oscillating signal applied to PMU 42.

Figure 8:
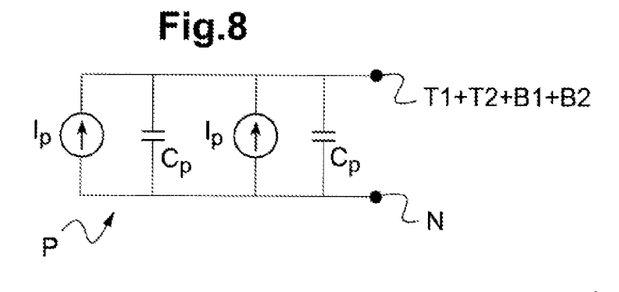
FIGS. 8, 9 and 10 illustrate three possible equivalent electrical configurations, respectively series, parallel and series-parallel, according to different possible choices of switching of the PZT electrodes.
Figure 9:
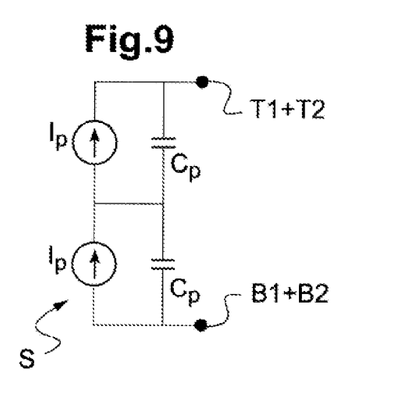
Figure 10:
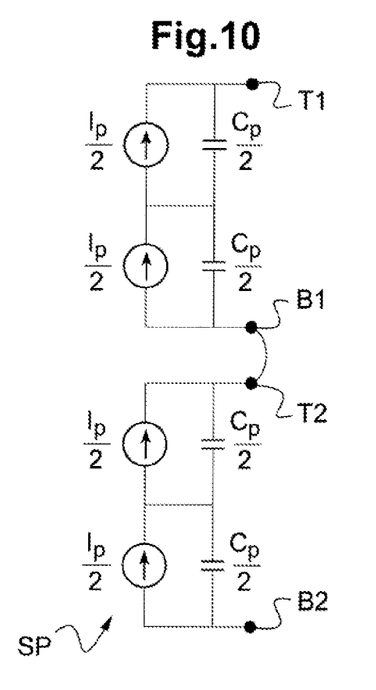

FIGS. 8, 9 and 10 hence illustrate three possible configurations, respectively parallel, series and series-parallel, which can be obtained by modifying the coupling of the electrodes between each other.

For these different figures, Ip represents the current sent by each PZT layer 52, equated to a current generator, and CP the internal capacitance of this current generator.

In parallel configuration P illustrated in FIG. 8, the two current source consisted by each of the two PZT layers 52 are arranged in parallel, like their internal capacitors. This parallel configuration P is equivalent to a current source 2·Ip, hence twice that of a monomorphous beam having only one PZT layer 52 on core 50), but on the other hand with a produced voltage that is half that of a monomorphous beam due to the doubling of the internal capacitance.

In series configuration S of FIG. 9, the connection to the core is not used and the two PZT layers 52 are connected in series. This provides a current source Ip, identical to what would be produced by a monomorphous beam; on the other hand, the two capacitors Cp being connected in series, the equivalent capacitance is divided by two and hence the output voltage is twice that of a monomorphous beam.

The series-parallel configuration illustrated in FIG. 10 uses the splitting of the surface electrodes into sub-electrodes T1, T2, respectively B1, B2, illustrated in FIGS. 6 and 7. This configuration is equivalent to a current source Ip/2 having an internal capacitance Cp/8. With respect to a monomorphous beam, the produced current is twice lower but the voltage is eight times higher due to the reduction of the internal capacitance.

As regards the produced power, it is demonstrated that it is the same in the three illustrated configurations, and that it is equal to twice the power that would be produced by a monomorphous beam.

In other words, nor the splitting of the electrodes into sub-electrodes, nor the type of coupling configuration used (series, parallel, or series-parallel) modifies the theoretical maximum effective power that the PEH is able to produce. Only the value of the current output by the PEH and that of the internal capacitance of the current source, and hence the output voltage of the PEH, change.

Figure 11:
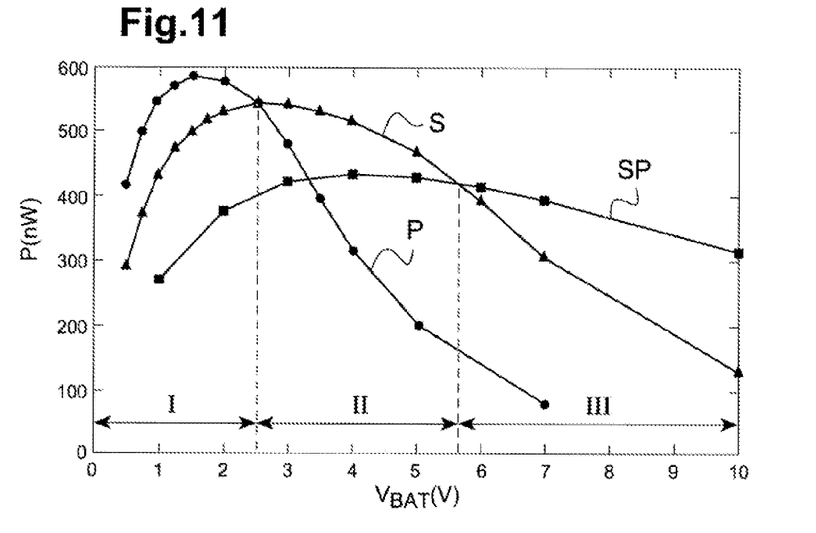
FIG. 11 illustrates three characteristics describing the variation of the effective power collected by the PEH as a function of the voltage at the battery terminals, for each of the three configurations of FIGS. 8, 9 and 10.

FIG. 11 illustrates three characteristics describing the variation of the efficient power produced by the PEH as a function of the voltage VBAT at the battery terminals, for each of the three series, parallel or series-parallel configurations of FIGS. 8, 9 and 10.

As can be seen, for each of the configurations S, P and SP, the curve passes by a maximum then progressively decreases, the power maximum corresponding to the condition RL=I/☐Cp, RL being the impedance of the load on which is the power is produced and ☐ being the resonant pulse of the pendular unit.

On an ideal, resistive load, the optimum power would be, as explained hereinabove, the same whatever the chosen configuration. Concretely, this power is however affected by various charge losses (leakage current of the diodes, etc.) as well as various non-linearities due in particular to the fact that the load modifies the PEH oscillation regime by a damping effect at the highest output voltages.

Advantageously and characteristically of the invention, the coupling mode of the different pairs of electrodes (parallel, series or series-parallel) is selected as a function of the measured level VBAT of the battery voltage, so as to select that of the characteristics P, S or SP which is liable to maximize the power output by the PEH.

In the example of characteristics of FIG. 11, three ranges I, II and III can hence be defined:

Range I: for the lowest battery voltages, parallel configuration P is selected,

Range II: for the intermediate voltages, series configuration S is selected,

Range III: for the highest voltages, series-parallel configuration SP is selected.

Figure 12:
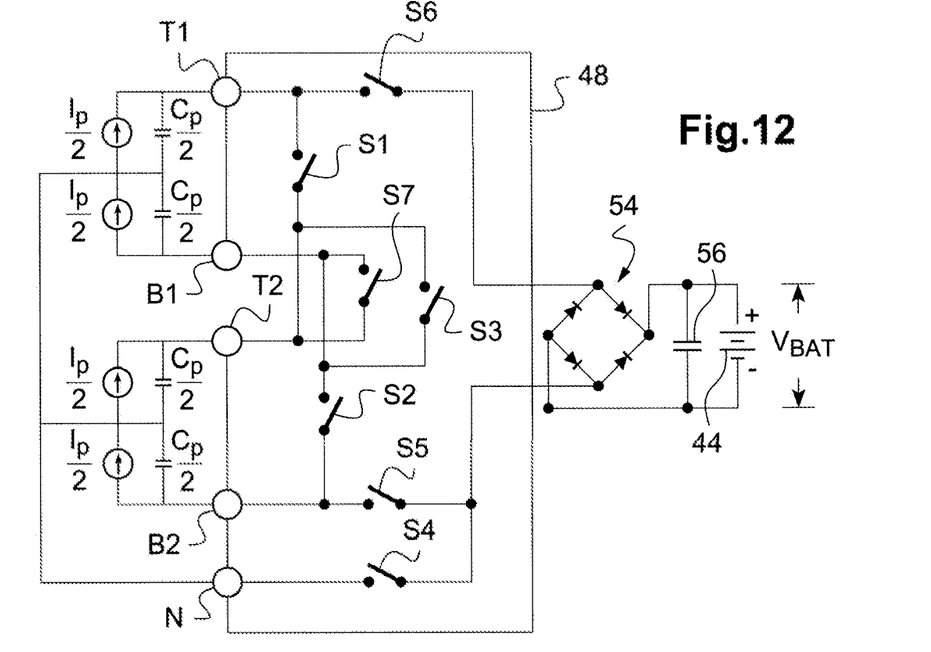
FIG. 12 is a synoptic diagram of the switching matrix operable for selecting the different configurations of FIGS. 8, 9 and 10.

FIG. 12 is a synoptic diagram of the switching matrix operable to select the different configurations of FIGS. 8, 9 and 10.

This switching matrix 48 is coupled to the different electrodes T1, T2, B1, B2 and N described hereinabove. It combines these different electrodes between each other by means of switches S1 . . . S7 and sends a combined (oscillating) signal to a battery charging PMU that, as in the illustrated example, can be reduced to its simplest terms, with a Full-Wave Bridge Rectifier or FBR 54, for example a Graetz bridge, and a filtering capacitor 56 coupled to the battery 44.

The open or closed states of the various switches S1 . . . S7 make it possible to selectively construct the parallel-series or parallel configurations illustrated in FIG. 10. Thus:

for series configuration S, the switches to be closed are: S1 (to couple T1 with T2 and form a single top electrode T=T1+T2), S2 (to couple B1 with B2 and form a single bottom electrode B=B1+B2), and S5 and S6 (to connect B and T, respectively, to bridge rectifier 54);

for parallel configuration P, the switches to be closed are: S1 (to couple T1 with T2 and form a single top electrode T=T1+T2, S2 (to couple B1 with B2 and form a single bottom electrode B=B1+B2), S3 (to connect in parallel T and B and form a single electrical reference T/B), S6 (to connect T/B to an end of the bridge rectifier) and S4 (to connect the other end of the bridge rectifier) to the neutral electrode N of shim 50);

for series-parallel configuration SP, which uses the splitting of the electrodes T1/T2 and B1/B2, the switches to be closed are: S5, S6 and S7.

Bridge rectifier 54 will begin to charge the battery when the open circuit voltage of the output signal of the switching matrix 48 will be higher than VBAT+2VD (VD being the voltage drop equal to the threshold voltage of the diodes of the bridge 54).

The opening or the closing of each of the switches S1 . . . S7 is controlled as a function of the voltage level VBAT of the battery:

if VBAT is comprised in range I of FIG. 11, then the switches that select parallel configuration P will be closed;

if VBAT is comprised in range II, series configuration S will be selected;

and for the higher voltages of VBAT, corresponding to range III, series-parallel configuration SP will be selected.

It will be noted that, voltage VBAT varying slowly, the transitions from one range to another, and hence the changes of configuration P, S or SP, will be relatively infrequent.

From the hardware implementation point of view, it is advantageous to use for the matrix switches S1 . . . S7 static switches whose main consumption (otherwise minimal) results from the conduction/cutoff state changes.

Figure 13:
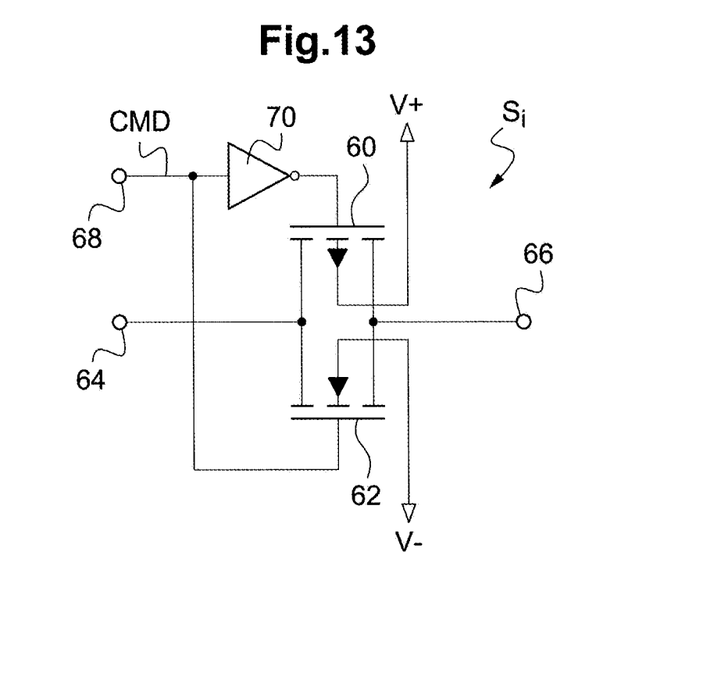
FIG. 13 is an example of static complementary MOS switch usable for implementing the switching matrix of FIG. 12.

FIG. 13 illustrates an example of such a static complementary MOS transistor switch usable for implementing switching matrix 48 of FIG. 12.

Each switch includes an input terminal 64 and an output terminal 66 coupled to each other by two complementary PMOS 60 and NMOS 62 transistors controlled by a CMD signal applied to a terminal 68 and inverted for one of the transistors by an inverter 70. The command signal CMD can be generated for example by the microcontroller 34, as soon as its level is higher than or equal to that of the voltage present on the terminals 64 and 66.

The consumption of such a switching matrix 48 is almost null, unlike the conventional circuits generally used by the PEH, implementing very complex ASICs such as those of the SSHI type mentioned in introduction.

The circuit simplification moreover allows a significant gain of surface on the printed circuit board of the leadless capsule, the PMU being, as can be seen, reduced thanks to the invention to its simplest terms as regards the components to be used.

From the dynamic operation point of view, for producing the command signals CMD of each switch S . . . S7, the single operation consists in comparing at regular intervals the voltage VBAT present at the battery terminals with two thresholds (those separating the ranges I/II and II/III, respectively) to (potentially) modify the configuration of the pairs of electrodes of the PEH that are coupled to each other.

It will be noted that, in the present description, the considered case is a transducer comprising five distinct electrical connection points T1, T2, B1, B2 and N, coupled in such a manner to define three equivalent electrical configurations S, P or SP.

This choice is however given only by way of example and must not in any way be considered as limitative, many other configurations being also conceivable within the framework of the invention, with a lower or higher number of connection points and/or a lower number of equivalent electrical configurations (for example, only S and P configurations, without it is required to split the electrodes), or a higher number (for example, four or five configurations, implementing a greater number of connection points), from the moment that these different configurations are dynamically and automatically switchable under the control of the implant processor as a function of one or several predetermined criteria.

Figure 14:
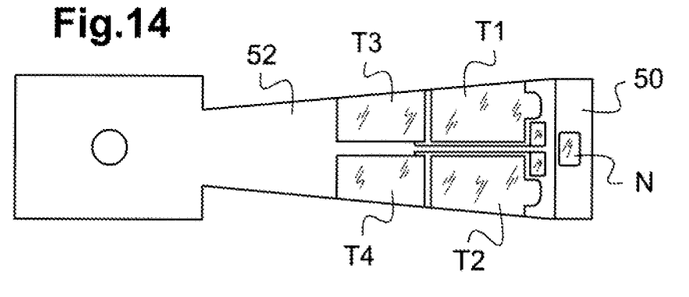
FIG. 14 illustrates, in plan view, an alternative of the PZT of FIGS. 6 and 7, in which each split surface electrode of the beam is itself divided into electrically independent sub-electrodes, which makes it possible to further increase the coupling combinations by the switching matrix.

Hence, FIG. 14 illustrates, in a plan view, an alternative of the PZT of FIGS. 6 and 7, in which each split surface electrode of the beam is itself sub-divided into electrically independent sub-electrodes, which makes it possible to further increase the coupling combinations by the switching matrix.

In this illustrated example, the top electrode is divided into four sub-electrodes T1, T2, T3 and T4, and likewise the bottom electrode is divided into four sub-electrodes B1, B2, B3 and B4.

Figure 15:
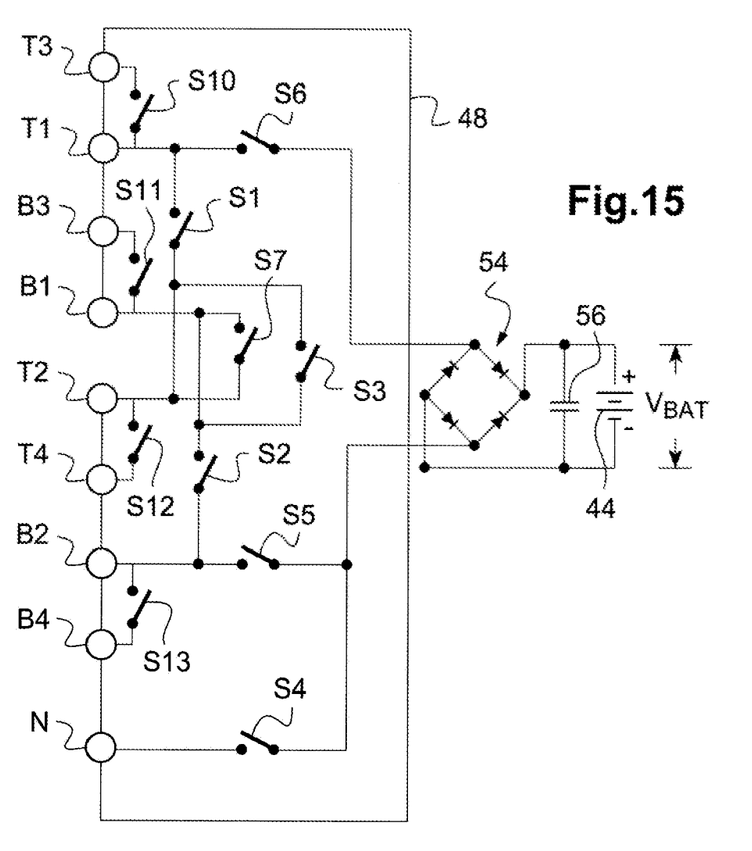
FIG. 15 is a synoptic diagram of a switching matrix adapted to the multi-sub-electrode PZT of FIG. 14.

FIG. 15 is a synoptic diagram of a switching matrix adapted to the multi-sub-electrode PZT of FIG. 14.

This switching matrix is coupled to electrodes T1, T2, T3, T4, B1, B2, B3, B4 and N and makes it possible to combine these different electrodes between each other by means of switches S1 . . . S13 to send a combined oscillating signal to a battery charging PMU, consisted for example, as illustrated, of a full-wave bridge rectifier or FBR 54 such as a Graetz bridge and a filtering capacitor 56 coupled to the battery 44.

The open or closed states of the switches S1 . . . S13 make it possible to obtain selectively a multiplicity of different functional configurations, such as:

parallel configuration: S1, S2, S3, S4 and S6 closed;
series configuration: S1, S2, S5 and S6 closed;
configuration with the use of the additional sub-electrodes: S5, S6 and S7 closed;
production of additional voltage (with a smaller power): S10, S11, S12 and S13 open (this configuration being combinable with the other configurations);
maximization of the produced power: S10, S11, S12 and S13 closed (wherein this configuration being here again combinable with the other configurations).

Figure 16:
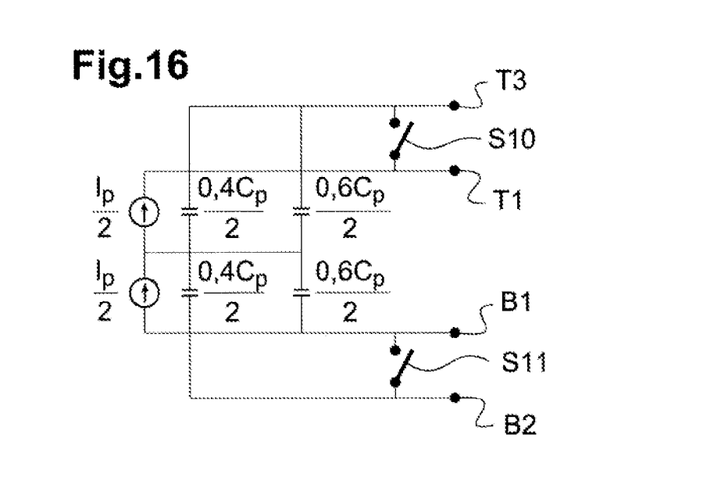
FIGS. 16 and 17 illustrate two additional equivalent electrical configurations made possible thanks to the multi-electrode PZT of FIG. 14.
Figure 17:
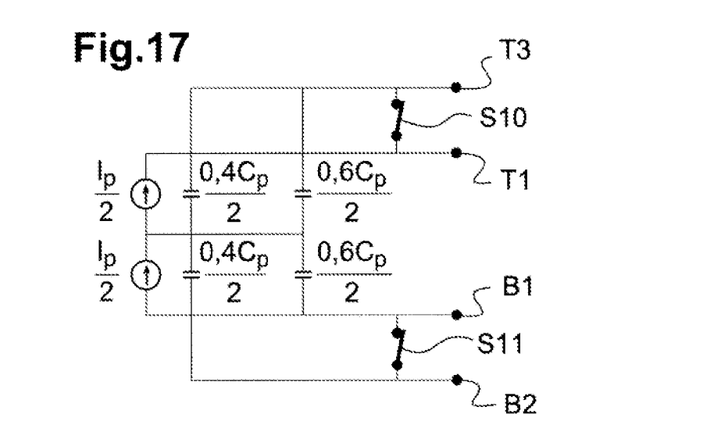

FIGS. 16 and 17 illustrate in particular two additional equivalent electrical configurations made possible in this example, for an opening and a closing, respectively, of the switches S10 and S11:

in the first case, the configuration is equitable to a current source Ip/2 having an internal capacitance 0.6 Cp/4 (hence an increased voltage due to the reduction of the internal capacitance), whereas in the second case, the configuration is equitable to a current source Ip/2 having an internal capacitance Cp/4 (T1 being in parallel with T3 and B1 being in parallel with B3). The output voltage is lower than in the preceding case, but the output power is higher.

Figure 18:
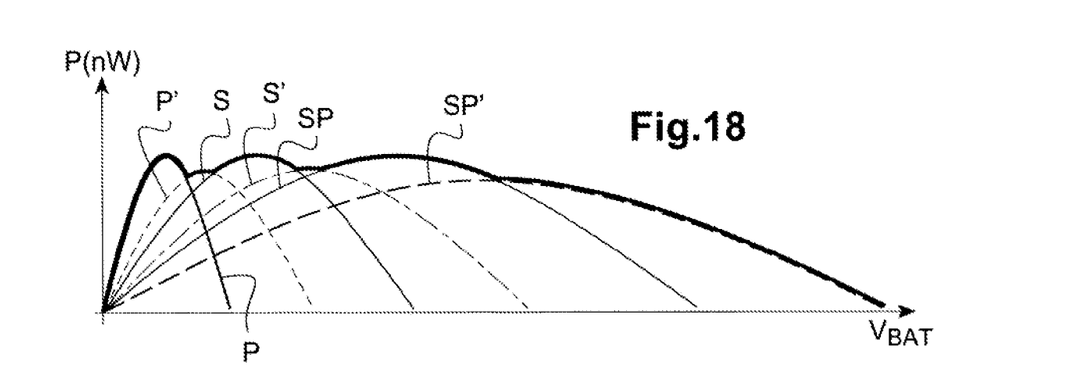
FIG. 18 illustrates six characteristics describing the variation of the effective power collected by the PEH as a function of the voltage at the battery terminals, for various configurations liable to be selected by the matrix of FIG. 15.

FIG. 18 illustrates six characteristics describing the variation of the efficient power collected by the PEH as a function of the voltage at the battery terminals.

With respect to FIG. 11 described hereinabove, the multiplication of the number of electrodes and hence of the number of switching possibilities allows increasing the number of selectable characteristics: further to the above-described series S, parallel P and series-parallel SP configurations (represented in solid line), the opening of the switches S10 and S11 creates corresponding additional configurations, S', P' and SP' (shown is dashed line), providing an additional voltage. As a function of the voltage level VBAT of the battery, it will then be possible, using suitable switching, to select the range offering the better power/voltage compromise.

Of note, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", and/or "including," when used in this specification, specify the presence of stated features, integers, steps, operations, elements, and/or components, but do not preclude the presence or addition of one or more other features, integers, steps, operations, elements, components, and/or groups thereof.

As well, the corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

The invention claimed is:

1. An energy harvesting module, comprising:
a pendular unit subjected to external stresses applied to the module, the pendular unit comprising a beam that is elastically deformable in bending according to at least one degree of freedom, with a clamped end and an opposite free end coupled to an inertial mass,
wherein the beam is a piezoelectric beam forming a mechanical-electrical transducer adapted to convert a mechanical energy produced by oscillations of the pendular unit into an oscillating electrical signal collected by electrodes; and
a power management circuit, adapted to rectify and regulate the signal collected by the electrodes, to output a stabilized direct power voltage or current,
wherein the piezoelectric beam carries a plurality of electrodes whose number and configuration define a plurality of pairs of electrodes between which a corresponding plurality of oscillating signals can be simultaneously collected,
and wherein the energy harvesting module further comprises, between the piezoelectric beam and the power management circuit, a switching matrix adapted, as a function of an input command, to selectively switch the plurality of pairs of electrodes between each other according to a plurality of different series, parallel and/or series-parallel configurations, to output a combined oscillating signal applied to the power management circuit,
wherein said input command is function of a voltage level signal of an energy storage component coupled to the power management circuit output and charged by said stabilized direct power voltage.

2. The module of claim 1, wherein the power management circuit is essentially consisted of a rectification stage and a filtering stage, said stages receiving as an input the combined oscillating signal output by the switching matrix and outputting said stabilized direct voltage or current.

3. The module of claim 1, wherein the piezoelectric beam is a bimorphous beam comprising a central conductive core and at least two surface electrodes on each side of the beam, the central conductive core and/or the surface electrodes being connected to the input of the switching matrix to selectively define pairs of electrodes combined to each other to produce said plurality of different series, parallel and/or series-parallel configurations.

4. The module of claim 1, wherein said at least two surface electrodes are subdivided into sub-electrodes that are selectively switchable by the switching matrix in complement to said series, parallel and/or series-parallel configurations, to modify the equivalent capacitance of said electrodes in order to produce an extra voltage or power at the switching matrix output.

5. The module of claim 1, wherein the switching matrix is consisted of individually controllable static switch components.

6. The module of claim 5, wherein the static switch components each comprise a pair of complementary PMOS/NMOS transistors that are symmetrically controlled in conduction or cutoff state.

7. The module of claim 1, further comprising a means for comparing the current voltage level of the energy storage component with at least two successive voltage level ranges, and wherein a transition of the current voltage level of the energy storage component from one range to another during the charge is operable to control a change of series, parallel and/or series-parallel configuration of the switching matrix.

8. The module of claim 1, wherein the successive ranges are advantageously ranges each corresponding to a respective series, parallel and/or series-parallel configuration maximizing the power returned by the piezoelectric beam.

9. The module of claim 1, wherein the module is incorporated to an autonomous device housing, within a device body: an electronic unit; said energy harvesting module; and an energy storage component for powering the electronic unit, and wherein said stabilized direct voltage or current output by the power management circuit is then used to power the electronic unit and/or to charge the energy storage component of the autonomous device.

10. The module of claim 9, wherein the autonomous device is an active medical device.

11. The module of claim 10, wherein the active medical device is an autonomous implantable capsule comprising a capsule body provided with an anchoring element for its anchoring to a wall of an patient's organ, and wherein said external stresses to which is subjected the pendular unit of the energy harvesting module are stresses applied to the capsule body under the effect of movements of said wall and/or blood flow rate variations in the surrounding environment.

* * * * *